(12) United States Patent
Lim et al.

(10) Patent No.: US 9,877,830 B2
(45) Date of Patent: Jan. 30, 2018

(54) HEART VALVE ASSEMBLY COMPRISING TWOFOLD SEALING

(71) Applicant: Venus Medtech (Hangzhou), Inc., Hangzhou, Zhejiang (CN)

(72) Inventors: Hou-Sen Lim, Regensburg (DE); Wolfgang Götz, Regensburg (DE)

(73) Assignee: Venus Medtech (Hangzhou) Inc. (CN)

( * ) Notice: Subject to any disclaimer, the term of this patent is extended or adjusted under 35 U.S.C. 154(b) by 0 days.

(21) Appl. No.: 15/126,168

(22) PCT Filed: Mar. 13, 2015

(86) PCT No.: PCT/EP2015/055362
§ 371 (c)(1),
(2) Date: Sep. 14, 2016

(87) PCT Pub. No.: WO2015/136104
PCT Pub. Date: Sep. 17, 2015

(65) Prior Publication Data
US 2017/0095326 A1    Apr. 6, 2017

(30) Foreign Application Priority Data
Mar. 14, 2014   (EP) .................................... 14160065

(51) Int. Cl.
*A61F 2/82*   (2013.01)
*A61F 2/24*   (2006.01)

(52) U.S. Cl.
CPC .......... *A61F 2/2418* (2013.01); *A61F 2/2439* (2013.01); *A61F 2250/006* (2013.01)

(58) Field of Classification Search
CPC ....................................................... A61F 2/82
See application file for complete search history.

(56) References Cited

U.S. PATENT DOCUMENTS

2006/0287717 A1   12/2006   Rowe et al.

FOREIGN PATENT DOCUMENTS

| CA | 2412063 | 5/2004 |
|----|---------|--------|
| WO | WO 2008/029296 | 3/2008 |

*Primary Examiner* — Matthew Schall
(74) *Attorney, Agent, or Firm* — Raymond Sun (57) ABSTRACT

The present invention relates to a heart valve assembly (1000), comprising a frame (1) and a heart valve (100), wherein the frame (1) supports the heart valve (100) or is interconnected thereto, preferably by sewing or sewing alone, the frame (1) comprising at least a first guiding structure (2a) for guiding at least one tension thread (5) for folding and/or unfolding the frame (1) around or along the frame (1), preferably at an outside or an outer circumference of the guiding structure (2a), wherein the heart valve (100), comprises at least two leaflets (101, 101', 101"); an interconnecting tissue (301) interconnecting the leaflets (101, 101', 101") with the frame; wherein the interconnecting tissue (301) or parts thereof, respectively, is interconnected to at least one of the guiding structures (2a, 2b) such that it covers the guiding structure (2a, 2b) or parts thereof at an inner circumference of the guiding structure (2a, 2b) and such that it also covers at least both an upper part (2c) and a lower part (2d) of the outer circumference of the guiding structure (2a, 2b).

8 Claims, 6 Drawing Sheets

HEART VALVE ASSEMBLY COMPRISING TWOFOLD SEALING

The present invention relates to a heart valve assembly according to claim 1.

From WO 2009/109348 A1, heart valve assembly or implants comprising a frame and a heart valve attached to the frame are known.

One object of the present invention is to provide another heart valve assembly comprising a heart valve.

This object may be solved by a heart valve assembly (also referred to as 'implant' herein) having the features of claim 1.

Hence, in accordance with the present invention, the heart valve assembly comprises a frame and a heart valve.

The frame supports the heart valve or is interconnected thereto, preferably by sewing or sewing alone.

The frame comprises at least a first guiding structure for guiding at least one tension thread for folding and/or unfolding the frame around or along the frame, preferably at an outside or an outer circumference of the guiding structure.

The frame further comprises at least a second guiding structure that is different from the first guiding structure, also for guiding at least one tension thread for folding and/or unfolding the frame around or along the frame, preferably at an outside or an outer circumference of the guiding structure.

Also, the frame comprises at least two, preferably three, posts. The posts are being arranged between the first and the second guiding structure. They may contribute in interconnecting the first and the second guiding structure with each other and/or to maintain the distance between them.

The heart valve comprises at least two heart valve leaflets. It also comprises at least one crown piece (also referred to as 'triangle' hereinafter) interconnected to the leaflets. The crown piece is intended to be interconnected, directly or indirectly, for example sewed, to the frame (also referred to as the support or the body of the implant or a stent by way of example hereinafter).

The heart valve further comprises a top cuff and a bottom cuff.

The crown piece, the top cuff and the bottom cuff are each rings or ring-shaped, and both the top cuff and the bottom cuff are interconnected with the crown piece.

The interconnecting tissue or parts thereof, respectively, is interconnected to at least one of the guiding structures such that it covers the guiding structure or parts thereof at an inner circumference of the guiding structure and such that it also covers both an upper part and a lower part of the outer circumference of the guiding structure.

In the following, the use of the expression "may be" or "may have", and so on, is to be understood synonymously with "in exemplary embodiments is" or "in exemplary embodiments has", respectively, and so on, and is intended to illustrate exemplary embodiments according to the present invention.

Exemplary embodiments according to the present invention are each also subject of dependent claims.

Exemplary embodiments according to the present invention may comprise one or more of the features named hereinafter.

In certain exemplary embodiments according to the present invention, at least one of the first and the second guiding structure comprises bars or consist of bars. The bars have top portions and bottom portions (herein, 'top' and 'bottom', like 'upper' and 'lower', refer to the orientation of the drawings or to the main orientation of the heart valve assembly or to the main flow through direction of the heart valve assembly in use). The interconnecting tissue or parts thereof are interconnected to the bars such that the interconnecting tissue covers the bars at an inner circumference of the guiding structure. It also covers the bars at both an upper part and a lower part of the outer circumference of the guiding structure.

In some exemplary embodiments according to the present invention, the interconnecting tissue comprises or consists of at least one crown piece interconnected to the leaflets, a top cuff and a bottom cuff each of which is ring-shaped, and both the top cuff and the bottom cuff are interconnected with the crown piece.

In certain exemplary embodiments according to the present invention, at least one of the top cuff and the bottom cuff is formed from a stripe or comprises a stripe, wherein the stripe is curved along its length.

In some exemplary embodiments according to the present invention, the top cuff has a width that is smaller than the width of the bottom cuff.

In certain exemplary embodiments according to the present invention, the crown piece or an section thereof is interposed between the top cuff and the bottom cuff.

In some exemplary embodiments according to the present invention, the frame is foldable and/or unfoldable.

In certain exemplary embodiments according to the present invention, bars of at least one of the first and the second guiding structure are interconnected to each other so as to form a zig-zag pattern or an undulating or meandering pattern. The bars are preferably arranged outside the circle or the area circumscribed by at least one of the interconnecting tissue, the top cuff and the bottom cuff.

In particular exemplary embodiments according to the present invention, the heart valve assembly or the frame may be folded or unfolded upon implantation by using one or several tension threads or filaments wound around the assembly.

In some exemplary embodiments according to the present invention, altering the shape of the implant means reducing or increasing a diameter, particularly an external diameter, of the implant. Such an alteration may or may not involve an alteration of the implant's length or any other kind of alteration.

In certain exemplary embodiments according to the present invention, folding the implant means reducing the diameter of the implant. Folding also covers "re-folding" of an once expanded implant.

In some exemplary embodiments according to the present invention, unfolding should be understood as increasing the diameter of the implant, or as expanding.

In certain exemplary embodiments according to the present invention, the diameter of the implant is arranged in a plane perpendicular to a main flow direction of the implant in case fluids flow through the implant after its implantation.

In some exemplary embodiments according to the present invention, at least one of the top cuff and the bottom cuff is formed from a stripe (or strap) or comprises a stripe (or strap, e.g. a thin band that is longer than broad). The stripe is (in its flat state) curved along its length, preferably or at least in a plane of its width.

In certain exemplary embodiments according to the present invention, the top cuff has a width that is smaller than a width of the bottom cuff.

In certain exemplary embodiments according to the present invention, the 'width' refers to an average width of the stripe.

In some exemplary embodiments according to the present invention, the top cuff and the bottom cuff are equally long (or almost equally long).

In particular exemplary embodiments according to the present invention, the top cuff is arranged closer to the leaflets than the bottom cuff.

In some exemplary embodiments according to the present invention, all leaflets are sewed to the crown piece by means of one or exactly one suture or stitch.

In particular exemplary embodiments according to the present invention, a suture is a filament or a thread or yarn. In these embodiments, 'one suture' means one filament (or thread or yarn) used for sewing two pieces together. In these embodiments, no second filament is used and, in consequence, only one knot is required.

In some exemplary embodiments according to the present invention, both the top cuff and the bottom cuff are sewed to the crown piece by means of one or exactly one suture.

In particular exemplary embodiments according to the present invention, the crown piece is sewed to the posts, preferably using (or via or through) through holes or eyelets of the posts, preferably through at least three or four, preferably consecutive through holes, preferably by means of tabs being small extensions of the crown piece or by leaving out the tabs, preferably by means of one or exactly one suture per post.

In some exemplary embodiments according to the present invention, the suture for interconnecting the crown piece to one post was started from an outer side of that post to an inner side of the post. Preferably, the single knot that interconnects both ends of the suture is arranged on an outside of the post.

In particular exemplary embodiments according to the present invention, the posts are arranged inside a circle or an area circumscribed by the crown piece.

In some exemplary embodiments according to the present invention, the posts are arranged outside the circle or the area circumscribed by at least one of the top cuff and the bottom cuff.

In particular exemplary embodiments according to the present invention, at least one of the first and the second guiding structure comprises or consists of bars that are interconnected to each other so as to form a zig-zag pattern or an undulating or meandering pattern. Neighbouring or adjacent or contacting bars are provided for moving relative to each other or for changing a distance or an angle between them (or between sections thereof, respectively) upon folding or unfolding of the implant or frame. The bars are preferably arranged outside the circle or the area circumscribed by at least one of the top cuff and the bottom cuff. In preferred embodiments according to the present invention the bars are covered on their inner side (being the side towards the inner space of the frame or implant) at least in part(s) by at least one of the top cuff and the bottom cuff.

In some exemplary embodiments according to the present invention, the leaflets have a first tab and a second tab arranged at opposite ends of the respective leaflet. The tabs are sewed onto the post of the frame.

In certain exemplary embodiments according to the present invention, the tabs extend from the body of the leaflet.

In particular exemplary embodiments according to the present invention, tabs of two adjacent leaflets are sewed to one post in an overlapping manner.

In certain exemplary embodiments according to the present invention, the tab of a first leaflet is or was sewed onto a post first, and wherein the tab of a second leaflet was sewed onto both the tab of a first leaflet and the post the tab of the first leaflet had been sewed to, all in one running stitch or with one suture.

In some exemplary embodiments according to the present invention, the frame comprises exactly three posts.

In certain exemplary embodiments according to the present invention, the heart valve comprises exactly three leaflets.

In certain exemplary embodiments according to the present invention, the crown piece may have up to three sections that are triangle in shape (at least once the crown piece's free ends are put together such that the crown piece forms a ring).

In particular exemplary embodiments according to the present invention, the frame (or support or body) of the implant is made of or comprises a metal or a shape memory material.

In certain exemplary embodiments according to the present invention, the top cuff and the bottom cuff are originally separate pieces, directly or indirectly interconnected with each other by sewing.

In some exemplary embodiments according to the present invention, the crown piece may have sections ending in a tip of a triangle section of the crown piece or in a tab extending from the tip of the triangle, the tab having a free end (before being fixed to, for example, the leaflets).

In certain exemplary embodiments according to the present invention, the crown piece is interposed between the top cuff and the bottom cuff.

In certain exemplary embodiments according to the present invention, at least one of the top cuff and the bottom cuff is made from porcine pericardium or is a fabric.

In some exemplary embodiments according to the present invention, the leaflets are interconnected with, preferably glued or sewed to, the crown piece.

In some exemplary embodiments of the apparatus according to the present invention, the at least one tension thread is a thread. The thread may be a surgical suture thread or similar to it. The thread may have the shape of a rope, a filament or a cord. The thread may be designed as a chain having a plurality of engaging chain links.

In this specification, the term thread or tension thread may also define a plurality of threads or tension threads whenever a person skilled in the art recognizes the exchangeability of the terms.

In certain exemplary embodiments according to the present invention, the implant or its frame is permeable for fluids in its implanted state in its longitudinal direction. "Permeable" means that the fluid may flow through the implant, for example, through an inner lumen thereof.

In particular exemplary embodiments according to the present invention, the frame has features as described in WO 2011/063972 A1 or WO 2009/109348 A1 with respect to the frame. The respective disclosures of WO 2011/063972 A1 and WO 2009/109348 A1 are incorporated in its entirety into the present specification by reference.

In certain exemplary embodiments according to the present invention, the implant is configured to have or has tension applied to it by using at least one tension thread. The tension is preferably controlled by altering a length of the pulling device by which it extends out of the interior of the shaft or a catheter or sections thereof.

In some exemplary embodiments according to the present invention, at least one of the heart valve and the frame comprises exclusively, i.e. only, (one or more) materials that are MRI (short for: magnetic resonance imaging) compatible.

In certain exemplary embodiments according to the present invention, at least one of the heart valve and the frame comprises exclusively (one or more) materials that are not magnetic, ferromagnetic, or both.

In some exemplary embodiments according to the present invention, at least one of the heart valve and the frame does not comprise metal or any metal alloy.

In certain embodiments according to the present invention, at least one of the posts has at least two openings through which tension threads are guided from an inside or inner space of the implant to an outside of the implant and back from the outside to the inside. The tension threads are guided to the outside through a first opening of a first one of the posts and back to the inside—or vice versa—through any second first opening of any second post, the first opening being different from the second opening, and the first post being different from the second post.

Some or all exemplary embodiments according to the present invention may provide for one, several or all of the advantages named above and/or hereafter.

In some of the embodiments according to the present invention, the interconnecting tissue or element forms two sealing tissues or elements. Having two such elements instead of only one has proven to contribute to achieving a superb sealing effect.

Since, as in certain embodiments according to the present invention, the sealing elements are ring-shaped structures which circumference is supported by only the tips of bars forming an undulating pattern without any support by the frame between the sealing elements' contact with the tips of the bars, the sealing elements are free to adapt to the native tissue surrounding the heart valve assembly. This way, sealing may be improved when compared to the results achieved by the state of art hitherto.

According to the present invention, the top cuff and the bottom cuff may have different widths. If the top cuff and the bottom cuff is now everted to the outside face of the bars both at an upper end and an lower end of the bars by an equal distance, a suture interconnecting the two cuffs (plus the crown piece) will not be positioned in a middle line of the bars. That way, the suture will not be damaged by the bars in a folded state of the implant in which the middle of the bars will usually have to face the highest pressure. At the same token, the suture does not contribute to applying pressure on the leaflets starting about the height of the bars of the guiding structure as the suture will not contribute to narrowing the space about the middle line of the bars due to its position beyond the middle line.

Further, sewing parts by just one suture may contribute in avoiding knots which in turn require space and are prone to damaging neighboring structures such as leaflets.

If, as in particular embodiments according to the present invention, the inner side of the top cuff is interconnected to the outer side of the bottom cuff, the resulting geometrical shape will show a profile that extends with a middle portion thereof into the inner space it circumscribes. In a front cut the geometrical shape may be called concave. That shape may fit best to the also concave shape of the bent bars and the resulting concave shape of the guiding structure which is another advantage.

Providing at least one of the heart valve and the frame to be MRI compatible allows advantageously for controlling the location and orientation of the apparatus or the implant, or both, by MRI upon use of the apparatus or implantation of the implant. No heat, sparks or artifacts are generated during MRI because of the materials chosen for the frame or the heart valve.

In the following, examples of the present invention will be described with reference to the accompanying figures wherein similar or identical assemblies or elements are denoted by same reference numerals.

FIG. 1a through FIG. 1e show parts of a heart valve 100 of a heart valve assembly according to a first exemplary embodiment of the present invention.

Figure 1A:
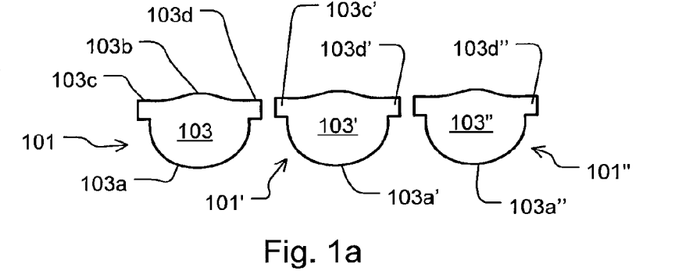
FIG. 1a shows three leaflets of a heart valve of a heart valve assembly according to a first exemplary embodiment of the present invention.

FIG. 1a shows three leaflets 101, 101' and 101" of the heart valve 100 of the first exemplary embodiment of the present invention. Instead of three leaflets 101, 101' and 101" the heart valve 100 according to the present invention may comprise any other number of leaflets, for example two. In the exemplary embodiment of FIG. 1a, all leaflets 101, 101' and 101" are identical. In other embodiments according to the present invention, at least two of them may, however, be different from each other.

In the exemplary embodiment of FIG. 1a, each leaflet 101, 101', 101" has a body 103, 103', 103", respectively, having a round or curved bottom section 103a, 103a', 103" and a rim section 103b, 103b', 103b" opposing the corresponding curved section 103a, 103a' or 103a". The rim section 103b, 103b', 103b" extends into opposing tabs 103c, 103c', 103" and 103d, 103d', 103d" which form the outmost portions to the opposing sides of the respective body 103, 103' or 103" (i.e. left and to the right of in the illustration of FIG. 1a).

Figure 1B:
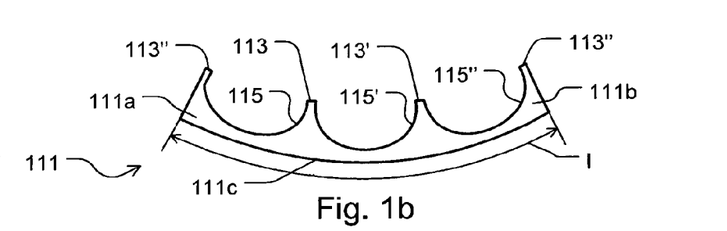
FIG. 1b shows a crown piece of a heart valve of a heart valve assembly according to the first exemplary embodiment of the present invention.

FIG. 1b shows a crown piece 111 of the heart valve 100. In use, the crown piece 111 is formed to a ring by connecting together the free ends 111a and 111b of the stripe shown in FIG. 1b with each other.

The crown piece 111 optionally comprises small tabs 113, 113', 113" and round portions 115, 115' 115".

The round portions 115, 115' 115" are shaped such that their curved rims correspond to the curved sections 103a, 103a' or 103a" of the leaflets 101, 101', 101".

In FIG. 1b, the reference number 113" is used twice. In practice, both small (half-)tabs 113" will contact each other so as to form one single small tab afterwards.

Figure 1C:
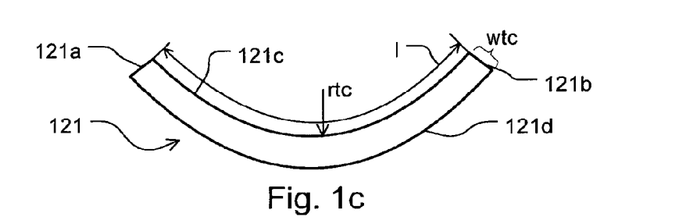
FIG. 1c shows a top cuff of a heart valve of a heart valve assembly according to the first exemplary embodiment of the present invention.
Figure 1D:
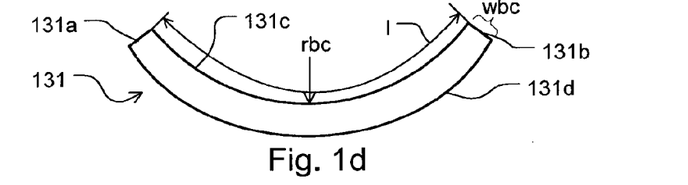
FIG. 1d shows a bottom cuff of a heart valve of a heart valve assembly according to the first exemplary embodiment of the present invention.
Figure 1E:
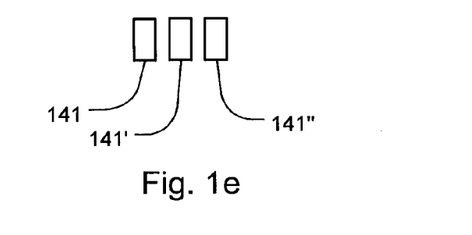
FIG. 1e shows three pledges of a heart valve of a heart valve assembly according to the first exemplary embodiment of the present invention.

In certain embodiments according to the present invention, the leaflets 101, 101' and 101" and/or the crown piece 111 (and, if applicable, also the pledges (also referred to a pledgets, these terms being, hence, synonyms) 141, 141', 141", see FIG. 1e) are cut (e.g. laser cut) from a (e.g. jib-fixed) bovine pericardium having a preferred thickness between 0.35 and 0.55 mm.

In some embodiments according to the present invention, the leaflets 101, 101' and 101" are all of identical or similar stiffness.

FIG. 1c shows a top cuff 121 of the heart valve 100. As can be seen from FIG. 1c, the top cuff 121, which is used in a ring-shaped form after having united the top cuff's ends 121a and 121b with each other, is formed from a flat stripe. The same applies to a bottom cuff 131 discussed below with reference to FIG. 1d showing a bottom cuff 131 with ends 131a, 131b of the heart valve 100 according to the first exemplary embodiment of the present invention.

The width of the top cuff 121 is denoted with wtc. The width of the bottom cuff 131 is denoted with wbc. In certain embodiments according to the present invention, wtc is smaller than wbc.

The length of the top cuff 121 is denoted with l. The width of the bottom cuff 131 is denoted with l as well since in the exemplary embodiment shown in the figures the top cuff 121 and the bottom cuff 131 are of the same length, at least with respect to a first side 121c of the top cuff 121 and a second side 131c of the bottom cuff 131. "l" also denotes the length of the lower rim or side 111c of crown piece 111. All lengths denoted with l are identical in certain embodiments according to the present invention.

The reference numerals rtc and rbc of FIGS. 1c and 1d denote the radius of the curvature of the top cuff 121 and the bottom cuff 131, respectively. The radius rtc and the radius rbc indicate that the stripes shown in FIGS. 1c and 1d are not straight but bent within the drawing plane of FIGS. 1c and 1d. rtc and rbc may be identical, without being limited hereto.

The inner side of top cuff 121 is denoted with 121c, the outer side with 121d.

The inner side of bottom cuff 131 is denoted with 131c, the outer side with 131d.

Because of the radius of top cuff 121 and bottom cuff 131, their inner sides 121c, 131c are shorter than their outer sides 121d, 131d, respectively.

In particular embodiments according to the present invention, the inner side 121c of top cuff 121 is interconnected with the outer side 131d of bottom cuff 131. This way, the resulting structure will be generally cylindrical with a middle (or about middle) portion that protrudes into the inner space formed by the resulting structure.

In certain embodiments according to the present invention, top cuff 121 and the bottom cuff 131 are cut (e.g. laser cut) from a (e.g. surface-tension) porcine pericardium having a preferred thickness between 0.15 and 0.25 mm.

The small tabs 113, 113', 113" may be used for a temporary stitch for temporarily securing the crown piece 111 to the frame 1. Both the provided temporary stitch and the small tabs 113, 113', 113" may be cut off and disposed later on.

FIG. 1e shows three pledges 141, 141' and 141" of the heart valve 100 according to the first exemplary embodiment of the present invention. The pledges 141, 141' and 141" are optional. The benefit of the potential pledges 141, 141' and 141" are discussed with regards to FIGS. 6a to 6c. The number of the pledges may correspond to the number of posts 3.

The heart valve assembly (also referred to as medical implant) according to some embodiments of the present invention comprises a heart valve 100, for example the one discussed with reference to FIG. 1a to 1d or 1e and a frame 1 or supporting structure, for example the one discussed with reference to FIGS. 2 and 3. In certain embodiments according to the present invention, the medical implant consists of the heart valve 100 and the frame 1.

Figure 2:
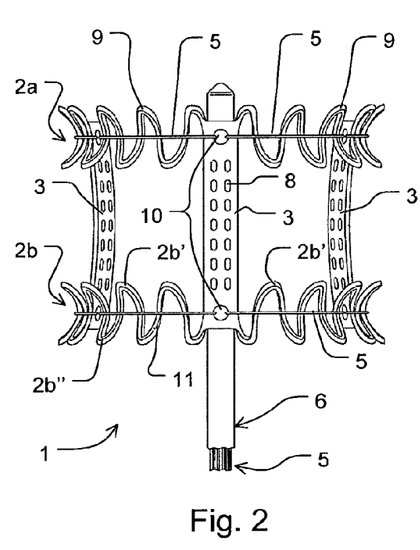
FIG. 2 shows a heart valve assembly according to the present invention in an expanded state which is expandable and can be reduced in its diameter by use of a means.

FIG. 2 shows a frame 1 of an exemplary heart valve assembly according to the present invention. The frame 1 is expandable and can be reduced again in its diameter. The diameter refers to a plane perpendicular to a longitudinal axis of the frame 1. The longitudinal direction also corresponds to the direction of the extension of the catheter 6 shown in FIG. 2.

Frame 1 comprises at least a first or upper—preferably circular—guiding structure or ring 2a and a second or lower—preferably also circular—guiding structure 2b. The guiding structures 2a, 2b are connected to rods or posts 3. In some embodiments, the guiding structures 2a, 2b can—additionally or alternatively or exclusively—fulfill the function of guiding structures for reins 5. The reins 5 form part of a catheter 6 and serve for applying force or tension or stress, respectively, to the guiding structures 2a, 2b for the purpose of expanding or folding the frame 1 in a targeted manner. In the example of FIG. 2, the guiding structures 2a, 2b are each designed having the shape of an outwardly half-open channel through which the reins 5 are guided. The half-open channel is opened in a direction away from the centre of the frame 1. However, the channel can also be shaped to be open to the heart valve assembly or to any other direction.

In the example of FIG. 2, the guiding structures 2a, 2b are interrupted by posts 3, i.e. the posts 3 are integrated into the guiding structures 2a, 2b such that they form sections of the guiding structures 2a, 2b.

In the embodiment of the frame 1 according to the invention shown in FIG. 2, the posts 3 and/or the guiding structures 2a, 2b have (round or differently shaped, e.g., oval, rectangular, elliptic, and so on) passage means or apertures 10. In the embodiment shown in FIG. 2, they serve as a passage for the reins 5. The posts 3 also have through openings 8, for example eyelets, which can be arranged in two parallel rows as in FIG. 2, in one row as in FIGS. 4a to 4c, or in any other arrangement.

Furthermore, the frame 1 can also comprise a number of guiding means 2a, 2b other than two, for example, one, three, four or more guiding means.

The guiding structures 2a, 2b can be arranged circularly, however, they can also be arranged non-circularly.

The guiding structures 2a, 2b can be formed integrally with the heart valve assembly; however, they can also be fabricated separately.

The guiding structures 2a, 2b can have the shape of a wave or undulation, respectively; however, they can also be fabricated in any other form, in particular, a non-wavy or non-undulating form.

Independent of all other features, frame 1 or parts thereof can be fabricated from flat material, e.g., a material which has been cut with a laser, wherein, e.g., after having designed a pattern in the flat material, the material is reformed into a tube (optionally by connecting, such as welding, longitudinal sides of the former flat material lane or web, respectively). However, frame 1 can also be fabricated from a tubular material directly.

The guiding structures 2a, 2b of frame 1 comprise or consist of a plurality of bars 11 which are each connected to another by means of connecting sections 9. The plurality of bars 11 may be arranged in a zig-zag pattern or an undulating or meandering pattern as is exemplary shown in FIG. 2.

Figure 3:
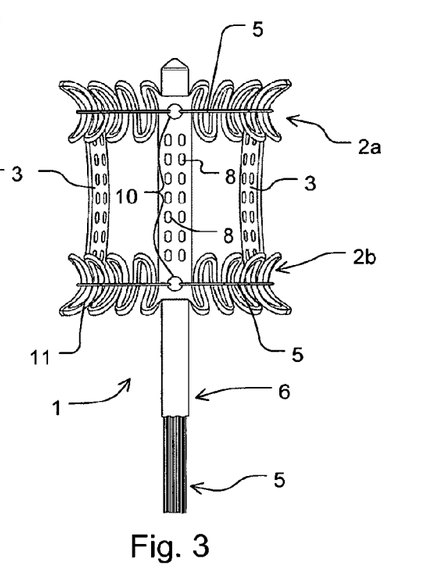
FIG. 3 shows the heart valve assembly of FIG. 2 in a non- or less expanded state.

FIG. 3 shows the frame 1 of FIG. 2. Two reins 5 have been led or guided around the frame 1 and return back to the catheter 6 through the respectively same passage means or apertures 10. The reins 5 apply a tension or stress on the frame 1, and, in consequence, frame 1 is not completely expanded or unfolded. Rather, the diameter of the frame 1 has been reduced or is being hindered from expanding in a free manner.

At least one of the top cuff 121 and the bottom cuff 131 can be secured to the bars 11 of the second or lower guiding structure 2b, for example by using a whip stitch, with, e.g. four stitches per bar 11, preferably evenly spaced. At the top portions of bars 11, indicated by 2b' in FIG. 2 and FIG. 3, and/or at the bottom portions of bars 11, indicated by 2" in FIG. 2 and FIG. 3, the curved bottom sections 103a, 103a', 103a" of the leaflets 101, 101', 101" may be additionally secured to the frame 1, for example once again by means of one or more surgeon's knots. Care should be taken to secured the body 103a, 103a', 103a" only at its rim or seam section.

Figure 4:
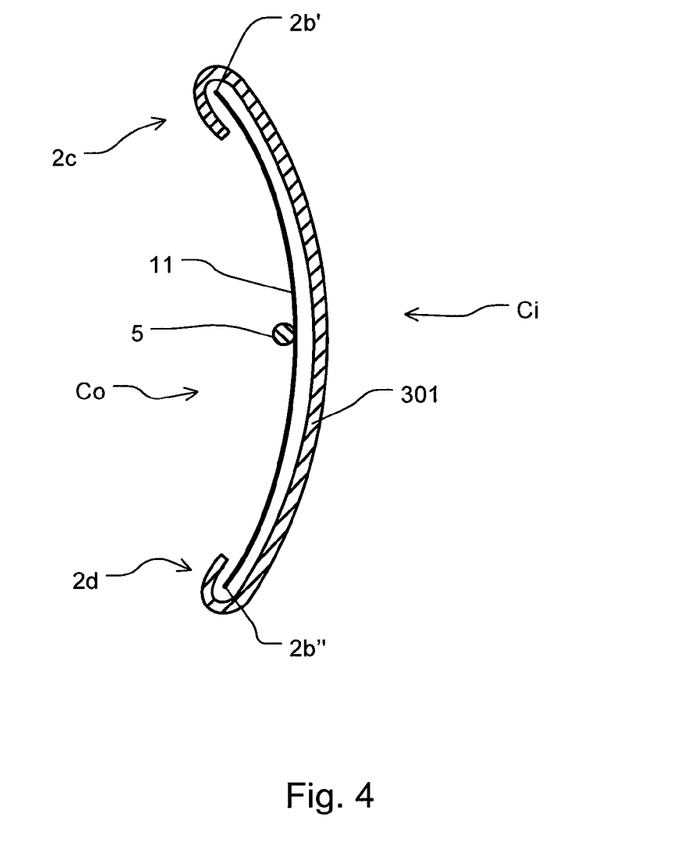
FIG. 4 shows one bar that is shown at the left-hand border of the second guiding structure shown in FIG. 2 in one embodiment.

FIG. 4 shows the bar 11 that is shown at the left-hand border of the second guiding structure 2b in FIG. 2. Although not parallel to the drawing plane, no part of bar 11 is not cut in FIG. 4.

In FIG. 4, ci denotes the inner circumference the second guiding structure 2b and co the outer circumference of the latter. The bar 11 is shown in FIG. 4 from its side, and more or less in the position its takes in FIG. 2 as well.

In contrast to the illustration of FIG. 2, the second guiding structure 2b and hence also bar 11 is covered by an interconnecting tissue 301. Within the disclosure of the present specification, interconnecting tissue 301 may also be referred to a sealing tissue or element as in certain embodiments, sealing is one of the functions provided by that tissue.

Both the interconnecting tissue 301 and the tension thread 5, which runs over the bar 11 but not also over the interconnecting tissue 301, are cut in the illustration of FIG. 4.

As can be seen from FIG. 4, the interconnecting element or tissue 301 covers in the inner circumference ci of the second guiding structure 2b and, hence, in this exemplary embodiment also of bar 11. Additionally, it also covers an upper part 2c and a lower part 2d of the second guiding structure 2b at the outer circumference co thereof.

Figure 5:
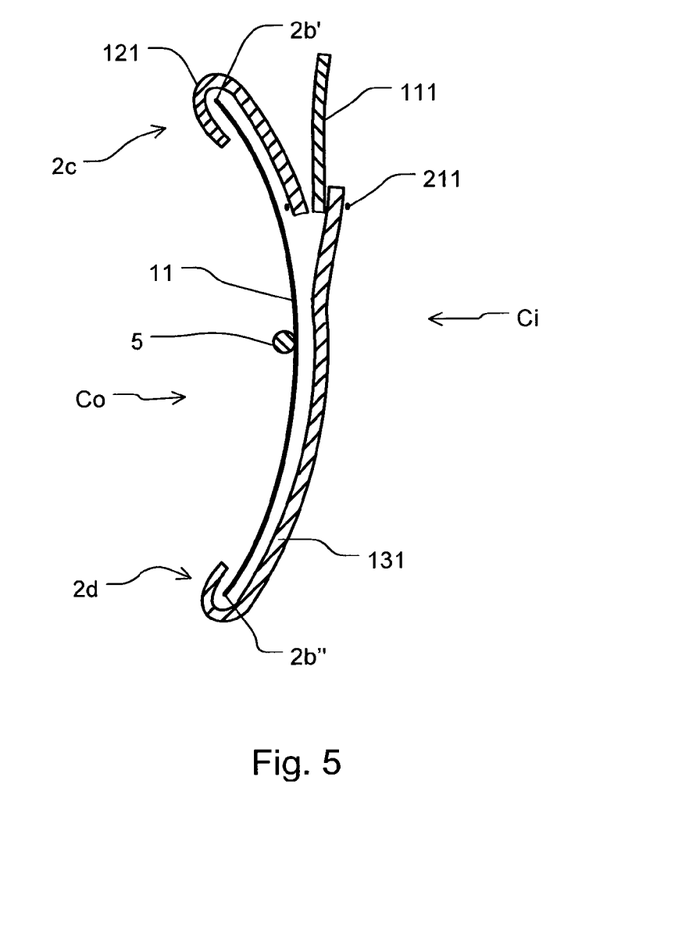
FIG. 5 shows one bar that is shown at the left-hand border of the second guiding structure shown in FIG. 2 in another embodiment.

FIG. 5 shows the bar 11 of FIG. 4. As in FIG. 4, bar 11, being part of the second guiding structure 2b, is covered by the interconnecting tissue 301.

However, in the exemplary embodiment of FIG. 5, the interconnecting tissue 301 is comprised by or consists of the top cuff 121, the crown piece 111 and the bottom cuff 131.

In the exemplary embodiment of FIG. 5, the top cuff 121, the crown piece 111 and the bottom cuff 131 are all connected to each other by a suture 211. As can be seen from FIG. 5, in this exemplary embodiment, the top cuff 121 and the bottom cuff 131 are arranged at opposite sides of the crown piece 111.

Figure 6:
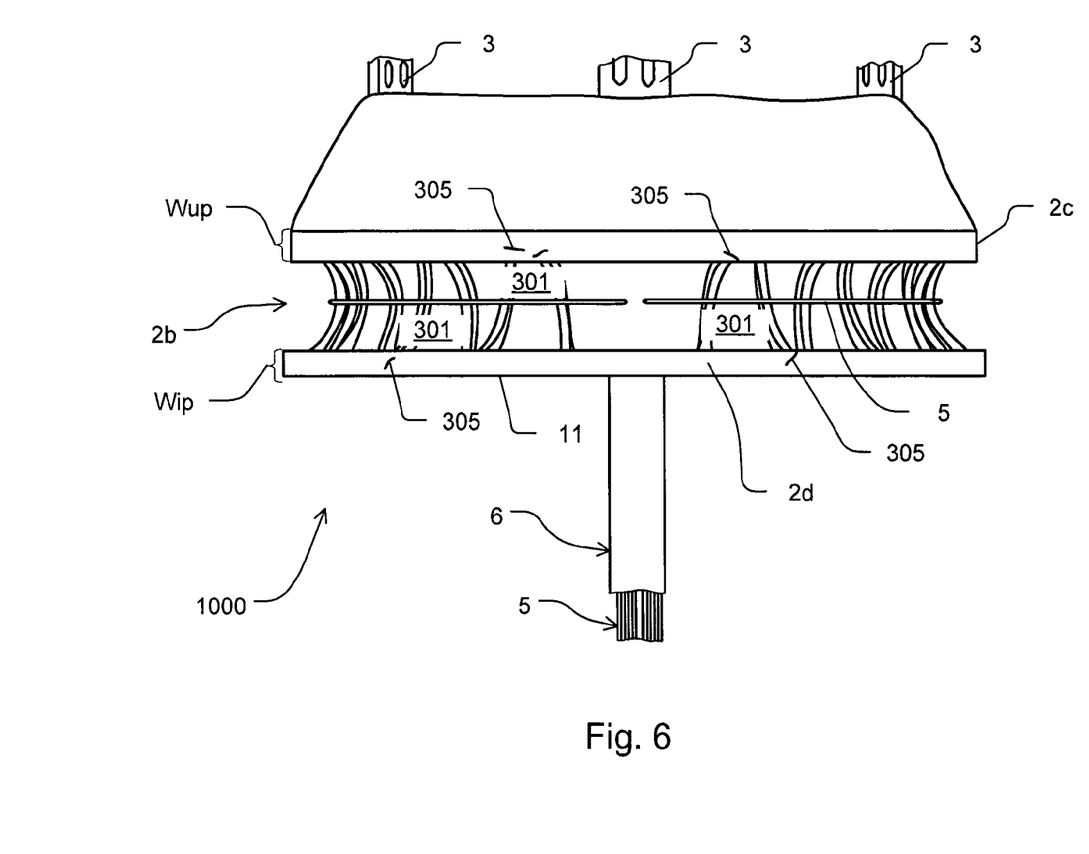
FIG. 6 shows the heart valve assembly (in parts) according to the present invention in one embodiment.

FIG. 6 shows the heart valve assembly 1000 according to the present invention in one embodiment. The reader looks onto the outer circumference co.

The heart valve assembly 1000 differs from what is shown in FIG. 2 by the interconnecting tissue 301 covering the outer circumference of the second guiding structure 2b by its upper part 2c and its lower part 2d. Hence, FIG. 5 also shows at least parts of the heart valve 100, namely the interconnecting tissue 301.

Both the upper part 2c and the lower part 2d may have a circular shape and, hence, cover the entire length of the second guiding structure 2b.

Both the upper part 2c and the lower part 2d may be interconnected to the top portions 2b' of bars 11 and the bottom portions 2b" as indicated by a number of sutures 305, a couple of which are shown in FIG. 5.

Both the upper part 2c and the lower part 2d may have a similar or identical width wup or wlp.

Both the upper part 2c and the lower part 2d may act as sealing devices or elements during use and seal between the heart valve 100 and the wall of the orifices into which the heart valve assembly has been inserted or implanted.

In FIG. 6, the lower parts of the posts 3 are covered by heart valve 100 material which also lines the bars 11 from the inside or lumen of the heart valve assembly 1000.

Figure 7:
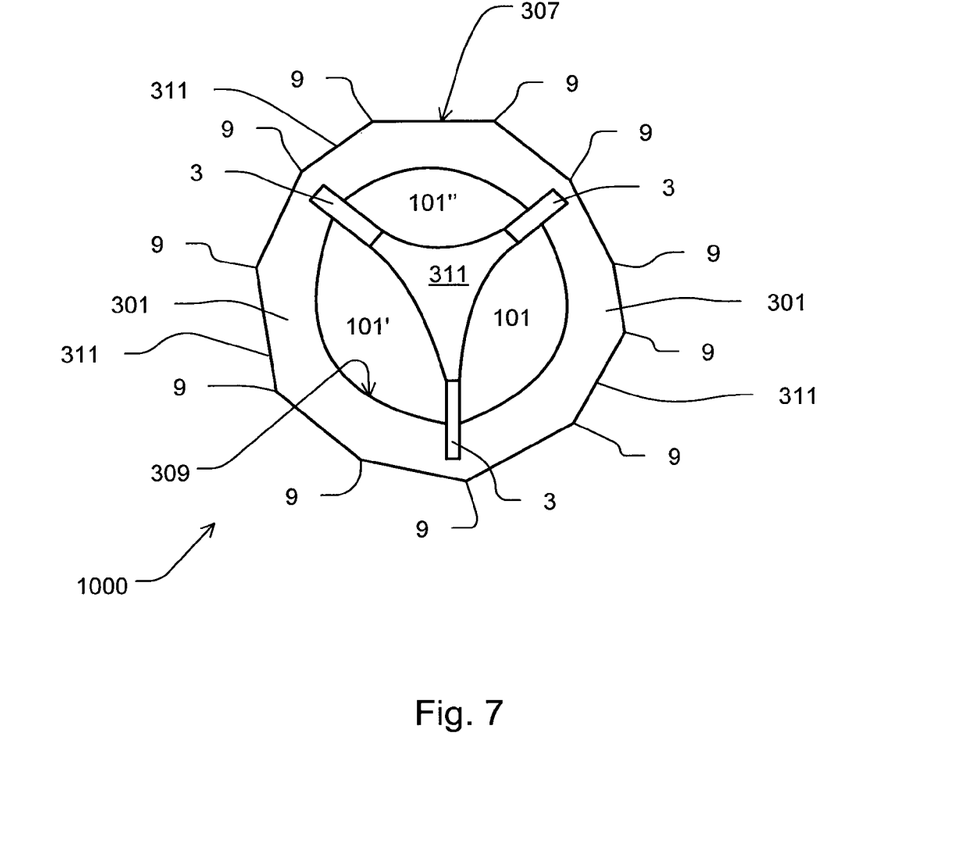
FIG. 7 shows the heart valve assembly according to the present invention in one embodiment in a bottom view.

FIG. 7 shows the heart valve assembly 1000 in a bottom view.

As can be seen, an open heart valve lumen 311, formed by the open leaflets 101, 101', 101" is surrounded by the leaflets and, further to an outside of the heart valve assembly 1000, also by the interconnecting tissue 301.

The outermost rim 307 of the interconnecting tissue 301 is, in contrast to an inner rim 309 thereof (corresponding to the lower part 2d), not round but has dentations or protrusions in the area of tips or interconnecting sections 9. Since the outermost rim 307 or the lower part 2d is not supported between neighbouring interconnecting sections 9 by any metal or otherwise hard structure of the frame 1 but comprises only relatively soft tissue, sections 311 of the outer rim 307 which are arranged between neighbouring interconnecting sections 9 are quite deformable. That way, the overwhelming portion of the outermost rim 307 or the upper and lower parts 2c, 2d of the interconnecting tissue 301 may contribute to sealing the heart valve assembly 1000 against the native heart tissue.

The expansion of frame 1 may benefit in the present exemplary embodiment from the internal stress or from shape-memory capacities of frame 1. The frame 1 may be manufactured from Nitinol or comprise such material.

REFERENCE NUMERALS

1 frame
2a first or upper guiding structure
2b second or lower guiding structure
2b' top portion of the bars or the second guiding structure
2b" bottom portion of the bars or the second guiding structure
2c upper part
2d lower part
3 posts
5 reins or tension thread(s)
6 catheter
8 through opening(s) or, as in particular embodiments; eyelet(s)
9 connecting sections or tip of bars
10 apertures
11 bars or struts
100 heart valve
101, 101', 101" leaflets
103 body of the heart valve 100
103a curved bottom section
103b rim section of the body of the leaflet
103c, 103d opposing tabs
111 crown piece
111a, 111b free end 111c lower rim or side of the crown piece
111e end of the lower rim or side of the crown piece
113, 113', 113" small tabs
115, 115' 115" round portions
121 top cuff
121a, 121b ends of top cuff
121c inner rim or side of top cuff
121d outer rim or side of top cuff
121e end of the inner rim or side of top cuff
131 bottom cuff
131a, 131b ends of bottom cuff
131c inner rim or side of bottom cuff
131d outer rim or side of bottom cuff
131e end of the inner rim or side of bottom cuff
141, 141', 141" pledges
211 suture interconnecting both the top cuff and the bottom cuff to the crown piece
301 interconnecting tissue
305 suture(s)
307 outermost rim
309 inner rim
311 sections
1000 implant or heart valve assembly (in parts)
ci inner circumference of the guiding structure
co outer circumference of the guiding structure
l length of the stripe
rtc radius
rbc radius
wtc width of top cuff
wbc width of bottom cuff
wup width of upper part
wlp width of lower part

The invention claimed is:

1. A heart valve assembly (1000), comprising a frame (1) and a heart valve (100), wherein:
the frame (1) supports the heart valve (100) or is interconnected thereto, the frame (1) comprising:
at least a first guiding structure (2a) for guiding at least one tension thread (5) for folding and/or unfolding the frame (1) around or along the frame (1);
at least a second guiding structure (2b), different from the first guiding structure (2a) for guiding at least one tension thread (5) for folding and/or unfolding the frame (1) around or along the frame (1);
at least two posts (3), the posts (3) being arranged between the first and the second guiding structure (2a, 2b) in order to interconnect the first and the second guiding structure (2a, 2b) with each other and/or to maintain the distance between them:
the heart valve (100), comprises:
at least two leaflets (101, 101', 101");
an interconnecting tissue (301) interconnecting the leaflets (101, 101', 101") with the frame;
wherein the interconnecting tissue (301) or parts thereof, respectively, is interconnected to at least one of the guiding structures (2a, 2b) such that it covers the guiding structure (2a, 2b) or parts thereof at an inner circumference of the guiding structure (2a, 2b) and such that it also covers at least both an upper part (2c) and a lower part (2d) of the outer circumference of the guiding structure (2a, 2b).

2. The heart valve assembly (1000) according to claim 1, wherein at least one of the first and the second guiding structure (2a, 2b) comprises bars (11) or consist of bars (11), wherein the bars (11) have top portions (2b') and bottom portions (2b'), and wherein the interconnecting tissue (301) or parts thereof is interconnected to the bars (11) such that it covers the bars (11) at an inner circumference of the guiding structure (2a, 2b) and also at both an upper part (2c) and a lower part (2d) of the outer circumference of the guiding structure (2a, 2b).

3. The heart valve assembly (100) according to claim 1, wherein the interconnecting tissue (301) comprises:
at least one crown piece (111) interconnected to the leaflets (101, 101', 101");
a top cuff (121); and
a bottom cuff (131);
wherein the crown piece (111), the top cuff (121) and the bottom cuff (131) each being ring-shaped, and each of the top cuff (121) and the bottom cuff (131) being interconnected with the crown piece (111).

4. The heart valve assembly (1000) according to claim 1, wherein at least one of the ring-shaped top cuff (121) and the ring-shaped bottom cuff (131) is formed from a stripe or comprises a stripe, wherein the stripe is curved along its length.

5. The heart valve assembly (1000) according to claim 3, wherein the top cuff (121) has a width (wtc) that is smaller than the width (wbc) of the bottom cuff (131).

6. The heart valve assembly (1000) according to claim 3, wherein the crown piece (111) or a section thereof is interposed between the top cuff (121) and the bottom cuff (131).

7. The heart valve assembly (1000) according to claim 1, wherein the frame (1) is foldable and/or unfoldable.

8. The heart valve assembly (1000) according to claim 1, wherein bars (11) of at least one of the first and the second guiding structure (2a, 2b) are interconnected to each other so as to form a zig-zag pattern or an undulating or meandering pattern, and wherein the bars (11) are arranged outside the circle or the area circumscribed by at least one of the interconnecting tissue (301), the top cuff (121) and the bottom cuff (131).

* * * * *